(12) United States Patent
Tripp et al.

(10) Patent No.: US 7,101,547 B1
(45) Date of Patent: Sep. 5, 2006

(54) METHOD FOR THE PREVENTION AND TREATMENT OF DISEASES CAUSED BY AN INFLAMMATORY RESPONSE MEDIATED BY ENDOGENOUS SUBSTANCE P BY USING ANTI-SUBSTANCE P ANTIBODIES

(75) Inventors: Ralph A. Tripp, Decatur, GA (US); Larry J. Anderson, Atlanta, GA (US); Deborah D. Moore, Marietta, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/889,317

(22) PCT Filed: Jan. 14, 2000

(86) PCT No.: PCT/US00/01032

§ 371 (c)(1),
(2), (4) Date: Jul. 13, 2001

(87) PCT Pub. No.: WO00/43040

PCT Pub. Date: Jul. 27, 2000

Related U.S. Application Data (60) Provisional application No. 60/116,835, filed on Jan. 22, 1999.

(51) Int. Cl.
*A61K 39/395* (2006.01)
(52) U.S. Cl. ............... 424/130.1; 424/133.1; 530/387.1; 530/388.24; 530/389.2
(58) Field of Classification Search ............. 424/130.1, 424/133.1; 530/387.1, 388.24, 389.2
See application file for complete search history.

(56) References Cited

U.S. PATENT DOCUMENTS

| | | | |
|---|---|---|---|
| 4,419,352 A | 12/1983 | Cox et al. | |
| 5,256,766 A * | 10/1993 | Coughlin | 530/327 |
| 5,332,817 A | 7/1994 | Desai et al. | |
| 5,340,822 A | 8/1994 | Emonds-Alt et al. | |
| 5,373,003 A | 12/1994 | Lowe, III | |
| 5,410,019 A | 4/1995 | Coy et al. | |
| 5,451,586 A | 9/1995 | Lowe, III | |
| 5,464,820 A | 11/1995 | Burton et al. | |
| 5,484,804 A | 1/1996 | Achard et al. | |
| 5,498,614 A | 3/1996 | Desai et al. | |
| 5,604,241 A | 2/1997 | Ito et al. | |
| 5,620,989 A | 4/1997 | Harrison et al. | |
| 5,688,806 A | 11/1997 | Desai et al. | |
| 6,034,105 A * | 3/2000 | Mendel | 514/337 |

FOREIGN PATENT DOCUMENTS

| | | |
|---|---|---|
| WO | WO 92/16547 | 10/1992 |
| WO | WO 96/29326 | 9/1996 |

OTHER PUBLICATIONS

Kudlacz, EM et al. Eur. J. Pharmacol. [1994] 270:291-300.*
Jafarian, A et al. Life Sciences [1995] 57(2):143-153.*
Larsen, GL. Clin. Resp. Physiol. [1986] 22(suppl. 7):35-37.*
Hemmingsson, P et al. Scand. J. Infect. Dis. [1993] 25(6):783-785.*
Moneret-Vautrin, DA et al. Rhinology [1992] 30(3):161-168.*
Agro et al., "Inhibition of Murine Intestinal Inflammation by Anti-Substance P Antibody," *Regional Immunology*, 5:120-126, 1993.
Couraud et al., "Anti-substance P Anti-idiotypic Antibodies," *Journal of Biological Chemistry*, 260(16):9461-9469, 1985.
Jafarian et al., "Passive Immunization with an Anti-Substance P Antibody Prevents Substance P-and Neurokin A-Induced Bronchospasm in Anesthetized Guinea-Pigs," *Life Sciences*, 57(2):143-153, 1995.
Maillet et al., "Anti-substance P anti-idiotypic antibodies modulate the secretory process in the rat parotid gland in vitro," *European Journal of Pharmacology*, 187:357-367, 1990.
Piccioli et al., Neuroantibodies: Ectopic Expression of a Recombinant Anti-Substance P Antibody in the Central Nervous System of Transgenic Mice, *Neuron*, 15:373-384, 1995.
Swenberg et al., "Development of an anti-idiotypic that blocks substance P primary antibodies and substance P membrane binding," *Brain Research*, 417:131-138, 1987.
Tripp et al., "Respiratory Syncytial Virus Infection and G and/or SH Protein Expression Contribute to Substance P, Which Mediates Inflammation and Enhanced Pulmonary Disease in BALB/c Mice," *Journal of Virology*, 74(4):1614-1622, 2000.

* cited by examiner

*Primary Examiner*—Christina Chan
*Assistant Examiner*—F. Pierre VanderVegt
(74) *Attorney, Agent, or Firm*—Klarquist Sparkman LLP (57) ABSTRACT

The present invention provides methods for preventing or treating a disease in a subject which is caused by an inflammatory response to a disease or syndrome which is mediated by endogenous substance P. These methods comprise the administration to the subject of a pharmaceutically-effective amount of anti-substance P antibodies, or anti-substance P antibody fragments, such as $F(ab)_2$ fragments, thereby inhibiting the activity of endogenous substance P in the subject. By inhibiting the activity of endogenous substance P in the subject, the levels of cytokines produced by T lymphocytes present in the subject are reduced, the signals which direct the inflammatory response to the infection become altered, and the amount of cytokine-induced inflammation becomes reduced. Respiratory syncytial virus is one example of an agent which causes an infection which often results in a disease caused by an inflammatory response to the infection mediated by endogenous substance P. Generally, from about 0.001 mg to about 10 g of anti-substance P antibodies, or anti-substance P antibody fragments, per kilogram of body weight per day are administered to a mammalian subject, with from about 1 mg to about 1000 mg of anti-substance P antibodies, or anti-substance P antibody fragments, per kilogram of body weight per day being preferred.

14 Claims, 3 Drawing Sheets

SEQUENCE LISTING

<160> NUMBER OF SEQ ID NOS: 2

<210> SEQ ID NO 1
<211> LENGTH: 11
<212> TYPE: PRT
<213> ORGANISM: Unknown

-continued

```
<220> FEATURE:
<223> OTHER INFORMATION: Neuropeptide

<400> SEQUENCE: 1

Met Leu Gly Phe Phe Gln Gln Pro Lys Pro Arg
1               5                   10

<210> SEQ ID NO 2
<211> LENGTH: 5
<212> TYPE: PRT
<213> ORGANISM: Unknown
<220> FEATURE:
<223> OTHER INFORMATION: Substance P receptor binding site
<221> NAME/KEY: DOMAIN
<222> LOCATION: (2)..(2)
<223> OTHER INFORMATION: Xaa = any amino acid

<400> SEQUENCE: 2

Phe Xaa Gly Leu Met
1               5
```

METHOD FOR THE PREVENTION AND TREATMENT OF DISEASES CAUSED BY AN INFLAMMATORY RESPONSE MEDIATED BY ENDOGENOUS SUBSTANCE P BY USING ANTI-SUBSTANCE P ANTIBODIES

PRIORITY CLAIM

This application is a U.S. national stage application of PCT/US00/01032, filed Jan. 14, 2000, which was published in English under PCT Article 21(2), which in turn claims the benefit of U.S. Provisional Application No. 60/116,835, filed Jan. 22, 1999.

BACKGROUND OF THE INVENTION

1. Field of the Invention

The present invention relates to methods for preventing and/or treating diseases caused by an inflammatory response mediated by endogenous substance P. The methods comprise the administration to a subject of a pharmaceutically-effective amount of anti-substance P antibodies, or anti-substance P antibody fragments, thereby inhibiting the activity of endogenous substance P. Such inhibition reduces the levels of cytokines produced by T lymphocytes, alters the signals which direct the inflammatory response to the infection, and reduces cytokine-induced inflammation. The present invention especially relates to methods for preventing and treating diseases caused by an inflammatory response to viral or bacterial infections. Moreover, the present invention especially relates to methods for preventing and treating diseases caused by an inflammatory response to respiratory syncytial virus.

2. Background

Inflammation. Inflammation is a localized, protective response of the immune system which is produced to protect a subject from disease. It is elicited by destruction of tissues, foreign substances such as allergens, infectious agents and cells such as viruses and bacteria. The inflammatory response destroys, dilutes or sequesters both the injurious agent and the injured tissue. It is characterized in the acute form by the classical signs of pain, heat, redness, swelling and loss of function. Histologically, it involves a complex series of events, including dilatation of arterioles, capillaries and venules, with increased permeability and blood flow, exudation of fluids, including plasma proteins, and leukocytic migration into the inflammatory focus.

T lymphocytes, which are products of lymphoid tissue, and their soluble protein products, known as cytokines, participate in humoral and cell-mediated immunity, and mediate the inflammatory response. T lymphocytes can suppress or assist the stimulation of antibody production in the presence of antigen, and can kill tumor and transplant tissue cells. Cytokines made by T lymphocytes, such as the intracellular cytokines interleukin-2 (IL-2), interleukin-4 (IL-4), interleukin-6 (IL-6) and interferon-γ (IFNγ), function to augment or suppress the immune response, or to change the type of immune response.

The immune-system-mediated inflammatory response, however, can also cause, or contribute to, disease, rather than prevent it. Some diseases, such as those caused by infection by respiratory syncytial virus appear to be caused in part by the inflammatory response. Small molecule anti-inflammatory agents which are currently employed to treat inflammation, disadvantageously have adverse side effects, such as gastrointestinal discomfort and decreased blood clotting efficiency. Steroid-based anti-inflammatory drugs also have adverse side effects, such as reduced adrenal gland function and generalized immune system inhibition.

Substance P. Substance P is a naturally-occurring, endogenously-released, undecapeptide which has multiple sites of action as a major pro-inflammatory neuromediator or neuromodulator, both in the central and peripheral nervous systems. Substance P is known to have regulatory effects upon several cell types present in the immune system, and to regulate the inflammatory response to foreign substances or pathogens by altering the expression of proinflammatory cytokines, which have been implicated in the pathogenesis of different neuropathologies. High levels of substance P have been implicated in the pathogenesis of diseases associated with inflammation. Substance P is also known to modulate the activity of cells affiliated with respiratory inflammation (neutrophils, mast cells and alveolar macrophages). Elevated concentrations of substance P and cytokines have been associated in the pathogenesis of a wide variety of diseases, including arthritis, experimental allergic encephalomyelitis, altered immunoregulation during human immunodeficiency virus infection, irritable bowel syndrome and airway hyperactivity.

Substance P has the following amino acid sequence (SEQ ID NO:1 in the Sequence Listing):

H-Arg-Pro-Lys-Pro-Gln-Gln-Phe-Phe-Gly-Leu-Met-NH$_2$, and belongs to a family of closely-related peptides known as the tachykinins (neurokinins), along with two other related, endogenously-released peptides, neurokinin A (NKA) and neurokinin B (NKB). Neurokinins are a group of structurally-related peptides characterized by a similar C-terminal pentapeptide that interacts with different receptor subtypes. The amidated C-terminal portion of the substance P neuropeptide is responsible for receptor binding (Otsuka et al., "Neurotransmitter Functions of Mammalian-Tachykinins," *Physiological Reviews* 73:229–307 (1993)). Substance P and neurokinin A are widely distributed in the airways and lungs of several species, including humans and guinea pigs.

Substance P is known to participate in inflammatory processes, and in the immune response, and appears to be involved in the process of neurogenic inflammation, pain transmission, regulation of blood pressure, inflammation processes and endocrine and exocrine secretion. Substance P has been strongly implicated in the transmission of pain, being coreleased alongside other transmitters and peptides, from small-diameter primary afferents. The primary role of substance P in neurogenic inflammation, smooth muscle contraction, and vasodilation is well established. In the central nervous system, where substance P and its receptors are widely distributed, its functional roles are less clear. Given parenterally, substance P and neurokinin A induce a variety of responses, including contraction of bronchial smooth muscle, mucus secretion, vasodilation, extravasation of plasma proteins and recruitment of inflammatory cells. The principal biological activity of these tachykinins resides in their structurally similar carboxyl sequence, . . . Phe-X-Gly-Leu-Met-COOH (SEQ ID NO. 2). Several binding experiments have shown that intestinal and vascular substance P receptors bind to the C-terminal pentapeptide of substance P. It has been suggested that the release of endogenous substance P and neurokinin A from pulmonary afferent C-fibers contributes to bronchial obstruction in asthma.

Specific membrane receptors for substance P have been found in neurons, and in muscular, glandular and immunocompetent cells, which helps to explain the diversity and importance of the physiological roles of substance P. Substance P effects its biological activity by ligation with these receptors, and the binding of substance P to its receptors enhances the incorporation of phosphate or inositol into phosphatidylinositol. Substance P, neurokinin A and neurokinin B appear to exert their biological effects primarily through interactions with three distinct receptors of the neurokinin family, named neurokinin receptor-1 (NK1), neurokinin receptor-2 (NK2) and neurokinin receptor-3 (NK3), respectively. Substance P affects antibody synthesis, or promotes cytokine production, through NK1 receptors which are well-characterized on T- and B-lymphocytes, monocytes and astrocytes, and possibly also via nonneurokinin receptors. While substance P preferentially binds to the NK1 receptor, its binding is not limited to this receptor. Further, the cationic, amphiphilic nature of the substance P molecule allows it to bypass the NK1 receptor and insert itself into the cell membrane, where it can directly interact with proteins. Thus, any inflammation-reduction therapy which targets the NK1 receptors (i.e., the use of compound or antibody NK1 receptor antagonists) will not fully inhibit the substance P pathway of inflammation, or be effective in preventing the pro-inflammatory actions of substance P.

The functional roles of substance P in the mammalian central nervous system and peripheral nervous system are currently being investigated by a variety of experimental approaches, including the use of antibodies and pharmacological agonists and antagonists. However, a continuous delivery of pharmaceutical drugs to the nervous tissue poses several practical problems, including limited diffusion and half-life of the drugs, secondary, non-specific effects of the drugs (because the endogenous neurokinins are preferential, but not selective agonists) and side-effects of the drugs. While studies have been performed with pharmaceutical antagonists of substance P receptors, studies in this area have been limited by the lack of efficacious antagonists specific for the NK1 receptors, and by the difficulty of using these antagonists in vivo, due to short half-lives, and the resulting lack of effect, and non-specific effects. Thus, the use of antibodies and antibody fragments which bind directly with substance P, as is done in the methods of the present invention, rather than using substance P receptor antagonists, is believed to be a preferable approach for inhibiting the action of endogenous substance P and, consequently for reducing the levels of cytokine production and cytokine-induced inflammation.

Additional information concerning substance P is present in the following publications: U.S. Pat. No. 4,680,283; Mantyh, "Substance P and the Inflammatory and Immune Response," *Annals of the New York Academy of Sciences* 632:263–271 (1991); Ho et al., "Substance P Modulates Human Immunodeficiency Virus Replication in Human Peripheral Blood Monocyte-Derived Macrophages," *AIDS Research & Human Retroviruses* 12:195 (1996); Kudlacz et al., "Parainfluenza Virus Type 3 Induced Alterations in Tachykinin NK1 Receptors, Substance P Levels and Respiratory Functions in Guinea Pig Airways," *European Journal of Pharmacology* 270:291 (1994); Yamawaki et al., "Viral Infection Potentiates the Increase in Airway Blood Flow Produced by Substance P," *Journal of Applied Physiology* 79:398 (1995); Ben-Jebria et al., "Effect of Passive Sensitization on the Mechanical Activity of Human Isolated Bronchial Smooth Muscle Induced by Substance P, Neurokinin A and VIP," *British Journal of Pharmacology* 109:131 (1993); Boichot et al., "Inhaled substance P Induces Activation of Alveolar Macrophages and Increases Airway Responses in the Guinea-Pig," *Neuropeptides* 25:307 (1993); Cheung et al., "Effects of Inhaled Substance P on Airway Responsiveness to Methacholine in Asthmatic Subjects In Vivo," *Journal of Applied Physiology* 77:1325 (1994); Heaney et al., "Substance P induces Histamine Release from Human Pulmonary Mast Cells," *Clinical & Experimental Allergy* 25:179 (1995); Murris-Espin et al., "Substance P and Alveolar Macrophages: Effects on Oxidative Metabolism and Eicosanoid Production." *Allergy* 50:334 (1995); Tomaki et al., "Elevated Substance P Content in Induced Sputum from Patients with Asthma and Patients with Chronic Bronchitis," *American Journal of Respiratory & Critical Care Medicine* 151:613 (1995); Yoshihara et al., "Involvement of Substance P in the Paroxysmal Cough of Pertussis," *Regulatory Peptides* 46:238 (1993); Ahmed et al., "Capsaicin Effects on Substance P and CGRP in Rat Adjuvant Arthritis," *Regulatory Peptides* 55:85 (1995); Jarrah et al., "Cholecystokinin-Octapeptide (CCK-OP) and Substance P(SP) Influence Immune Response to Cholera Toxin in Live Animals," *Advances in Experimental Medicine & Biology* 371A:563 (1995); Kincy-Cain et al., "Substance P-Induced IL-12 Production by Murine Macrophages," *Journal of Immunology* 158:2334 (1997); Palma et al., "Interleukin-6 Production by U373 MG, a Human Astrocytoma Cell Line; Different Pathways Involved in Substance P and Lipopolysaccharide Activation," *Journal of Immunology* 59:155 (1995); and Shadiack et al., "Lipopolysaccharide Induces Substance P in Sympathetic Ganglia Via Ganglionic Interleukin-1 Production," *Journal of Neuroimmunology* 49:51 (1994).

Respiratory Syncytial Virus. Respiratory syncytial virus is one example of an agent which causes an infection which, in turn, often results in a disease produced by an inflammatory response to the infection that may be mediated by endogenous substance P. The immune response to respiratory syncytial virus infection is characterized by the enhanced production of cytokines, increased levels of substance P, and bronchial inflammation. Respiratory syncytial virus is the most important cause of pneumonia and bronchiolitis in infants, and can result in death.

The only available treatment for respiratory syncytial virus is ribavirin, a purine nucleoside analog which inhibits the replication of a wide range of RNA and DNA viruses, and which has many disadvantages. The administration of ribavirin to patients in the form of an aerosol is costly and difficult, and limits its therapeutic efficacy. Furthermore, ribavirin antagonizes the activity of the antiviral agent zidovudine against human immunodeficiency virus type 1 (HIV-1), the causative agent of AIDS. When administered orally or intravenously, ribavirin causes anemia due to extravascular hemolysis and suppression of the bone marrow. Further, ribavirin is mutagenic in small animals, and the oral bioavailability of ribavirin is only about 45 percent. The long-term oral therapy of ribavirin is associated with both gastrointestinal and adverse symptoms in the central nervous system.

A need presently exists for an efficacious and convenient method for treating and preventing diseases which are caused by an inflammatory response mediated by substance P. Accordingly, the present invention provides an effective and convenient method for preventing and treating diseases caused by an inflammatory response to a variety of conditions that is mediated by substance P comprising inhibiting the activity of endogenous substance P with anti-substance P antibodies and/or anti-substance P antibody fragments. The data presented in the examples set forth below show that the inhibition of the biological activity of substance P with anti-substance P $F(ab)_2$ antibody fragments reduces the production of cytokines by T lymphocytes, thereby altering the signals which direct the inflammatory response to an infection caused by respiratory syncytial virus, and reducing potential cytokine-induced inflammation.

In accordance with the methods of the present invention, blocking the activity of endogenous substance P can potentially be employed to prevent or treat a wide variety of diseases or syndromes caused in whole or part by an inflammatory response mediated by substance P. Such diseases or syndromes include, by way of nonlimiting example, diseases ascribable to viral or bacterial infection such as infections associated with inflammatory bowel disease, virus-mediated bronchiolitis including that mediated by respiratory syncytial virus, bacterial colitis, inflammation associated with chlamydial diseases, lung injury associated with staphylococcal enterotoxin B, inflammation due to cytomegalovirus or hepatitis B virus, and sepsis, allergic diseases such as asthma, autoimmune diseases such as rheumatoid arthritis, pancreatitis, and inflammation associated with multiple sclerosis, and rejection of allografts and other transplanted tissues or organs. The prevention, reduction or elimination of the substance P-mediated inflammatory response can also be used to prevent adverse effects which may otherwise result from tissue or organ transplantation.

The administration of anti-substance P antibodies, or anti-substance P antibody fragments, to a subject to inhibit the activity of endogenous substance P is preferential to the administration of substance P NK1 receptor antagonists to the subject because, unlike substance P NK1 receptor antagonists, anti-substance P antibodies and anti-substance P antibody fragments inhibit the activity of substance P without receptor ligation, and before the substance P can cross the cell membrane in a receptor-independent manner.

DESCRIPTION OF THE RELATED ART

Cytokine Networks, Inc. and IDEC Pharmaceuticals are apparently developing products based on anti-macrophage inhibitory factor antibody technology. The inhibition of the cytokine macrophage inhibitory factor may represent a novel approach to the management of a variety of acute and chronic inflammatory diseases (Printout of company press release dated Sep. 9, 1997, provided and copyrighted by Business Wire Health Wire as downloaded from http://biz.yahoo.com/bw/97/09/09/idph_y000_0.html).

U.S. Pat. No. 5,688,806 describes spirocyclic piperidine derivatives which are stated to be substance P receptor antagonists. Such compounds were used in the treatment and prevention of inflammatory and central nervous system disorders.

Jafarian et al., "Passive Immunization with an Anti-Substance P Antibody Prevents Substance P- and Neurokinin A-Induced Bronchospasm in Anesthetized Guinea Pigs," *Life Sciences* 57:143–153 (1995), describe experiments to determine whether the intravenous administration of a monoclonal IgG-type anti-substance P antibody derived from the rat-mouse hybridoma NC1/34 to guinea pigs would alter pulmonary responses to endogenous substance P and neurokinin A. The passive immunization experiments were stated to confirm earlier reports which indicated that, in a guinea-pig model of asthma, active immunization against substance P reduced the bronchiospastic response to substance P, and to show that passive immunization of guinea pigs with a monoclonal anti-substance P antibody prevents the bronchiospastic effects of exogenous substance P and neurokinin A in vivo.

Piccioli et al., "Neuroantibodies: Ectopic Expression of A Recombinant Anti-Substance P Antibody in the Central Nervous System of Transgenic Mice," *Neuron* 15:373–384 (1995), describe the generation of transgenic mice that express recombinant antibodies against substance P under the control of the promoter of the neuronal vgf gene. The anti-substance P transgenic antibodies were stated to be effective in competing with endogenous substance P, as demonstrated by a marked inhibition of neurogenic inflammation by the antibodies in mice after neurogenic inflammation in the mice was produced by the application of mustard oil to the skin of the mice.

Swenberg et al., "Development of an Anti-Idiotypic Antibody that Blocks Substance P Primary Antibodies and Substance P Membrane Binding," *Brain Research* 417:131–138 (1987), describe the preparation of antibodies raised against substance P coupled to bovine albumin, and of substance P anti-idiotypic antibodies (antibodies raised against anti-substance P antibodies). This reference also describes the effects of substance P anti-idiotypic antibodies on substance P binding to both anti-substance P primary antibodies, and the substance P receptor in membrane preparations from rat duodenum, and the biological effect on substance P-induced spasmogenic responses.

Couraud et al., "Anti-substance P Anti-Idiotypic Antibodies, Characterization and Biological Activities," *Journal of Biological Chemistry* 260:9461–9469 (1985), describe the production of anti-substance P antibodies, and the production of anti-idiotypic antibodies which bind with substance P receptors, and which either mimic or block the physiological actions of substance P, depending upon the biological preparation.

Maillet et al., "Anti-substance P Anti-idiotypic Antibodies Modulate the Secretory Process in the Rat Parotid Gland in Vitro," *European Journal of Pharmacology* 187:357–367 (1990), describe the preparation of anti-idiotypic antibodies from rabbits in response to immunization with polyclonal anti-substance P antibodies, and the comparison of the effects of both anti-idiotypic antibodies and substance P on the rat parotid gland (a tissue in which substance P receptors have been well established).

None of the references cited above teaches or suggests the prevention or treatment of diseases caused by an inflammatory response to a viral or bacterial agent mediated by endogenous substance P by the administration of anti-substance P antibodies, or anti-substance P antibody fragments, to subjects.

SUMMARY OF THE INVENTION

The present invention provides effective and convenient methods for preventing or treating diseases in a subject caused by an inflammatory response mediated by endogenous substance P, especially a response to a viral or bacterial infection. The methods comprise administering to a subject a pharmaceutically-effective amount of anti-substance P antibodies, or anti-substance P antibody fragments, thereby inhibiting the activity of endogenous substance P in the subject. By inhibiting the activity of endogenous substance P in the subject, the levels of cytokines produced by T lymphocytes in the subject are reduced, and the signals which direct the inflammatory response to the viral or bacterial infection become altered, thereby reducing cytokine-induced inflammation. Generally, from about 0.5 mg to about 2 g of anti-substance P antibodies, or anti-substance P antibody fragments, per kilogram of body weight per day are administered to a mammalian subject, with from about 1 mg to about 1 g of anti-substance P antibodies, or anti-substance P antibody fragments, per kilogram of body weight per day being preferred. The methods of the present invention are particularly useful for preventing and treating diseases caused by an inflammatory response to an infection by respiratory syncytial virus.

BRIEF DESCRIPTION OF THE DRAWINGS

FIG. 2 shows a graph which plots the stimulation index in mean counts per minute (cpm) of stimulated cells over the mean counts per minute of unstimulated cultures for intact, $CD4^+$ and $CD8^+$ T lymphocytes which were stimulated with concanavalin, with or without the addition of various concentrations of substance P (in concentrations ranging from $10^{-5}$ M to $10^{-9}$ M), or which were left unstimulated in tissue culture medium, on the vertical axis, and the type of treatment on the horizontal axis, for the experiments described in Example 2. In FIG. 2, TCM indicates cells which were left unstimulated in tissue culture medium, CA indicates stimulation with concanavalin, open bars indicate intact T lymphocytes, black/white bars indicate $CD4^+$ T lymphocytes, and solid bars indicate $CD8^+$ T lymphocytes.

FIG. 3 shows a graph which plots the stimulation index of intact, $CD4^+$ and $CD8^+$ T lymphocytes which were stimulated with lipopolysaccharide, with or without the addition of various concentrations of substance P (in concentrations ranging from $10^{-5}$ M to $10^{-9}$ M), or were left unstimulated in tissue culture medium, on the vertical axis, and the type of treatment on the horizontal axis, for the experiments described in Example 2. In FIG. 3, TCM indicates cells which were left unstimulated in tissue culture medium, LPS indicates stimulation with lipopolysaccharide, open bars indicate intact T lymphocytes, black/white bars indicate $CD4^+$ T lymphocytes, and solid bars indicate $CD8^+$ T lymphocytes.

FIG. 4 shows a graph which plots the percent of intracellular (IC) cytokines produced by T lymphocytes in the bronchoalveolar lavage (BAL) fluid of BALB/c mice infected with respiratory syncytial virus collected 18 hours after the mice were treated with rabbit anti-substance P $F(ab)_2$ antibody fragments on the vertical axis, and the type of intracellular cytokine examined ($CD3^+$/IL-2, $CD3^+$/IL-4, $CD3^+$/IL-5, $CD3^+$/IL-6 and $CD3^+$/IFN$\gamma$) on the horizontal axis. This graph is based on the experiments described in Example 3. In FIG. 4, BAL indicates bronchoalveolar lavage fluid, diagonally stripped bars indicate 2 μg of anti-substance P antibody fragment, open bars indicate 20 μg of anti-substance P antibody fragment, open with black horizontal cross-hatching bars indicate 200 μg of anti-substance P antibody fragment, solid bars indicate treatment with 200 μg of normal rabbit Ig (nIg) antibody, and solid with white horizontal cross-hatching bars indicate no treatment (SHAM).

DESCRIPTION OF THE PREFERRED EMBODIMENTS

Definitions. For purposes of clarity, terms and phrases used herein are defined in the manner set forth directly below.

As used herein, "anti-substance P antibody" means any polyclonal or monoclonal antibody which inhibits the action of substance P. Such antibodies may be obtained from any species. They include, for example, monoclonal anti-substance P antibodies obtained from a mouse B cell hybridoma. In general, any class and subclass of antibody is effective in the present invention.

As used herein, "anti-substance P antibody fragment" means a portion of an anti-substance P antibody, as defined hereinabove, which is of a sufficient size and conformation to inhibit the action of substance P, and includes $F(ab)_2$ fragments of the antibody, wherein Fab represents the antigen binding Fragment. $F(ab)_2$ fragments are obtained by digestion of an immunoglobulin with pepsin. Fab fragments, conversely, are obtained by digestion of an immunoglobulin with papain. Both $F(ab)_2$ fragments and Fab fragments may be used to inhibit substance P. An advantage of using Fab and $(Fab)_2$ fragments is that they do not have the Fc fragment of the immunoglobulin molecule, and therefore will not bind to the Fc receptor present on some cells.

As used herein, the term "bind" means the well-understood interaction or other nonrandom association between antibodies, or antibody fragments, and antigens.

As used herein, the abbreviation "i.n." means that anti-substance P antibodies, or anti-substance P antibody fragments, were administered intranasally. As used herein, the abbreviation "i.p." means that anti-substance P antibodies, or anti-substance P antibody fragments, were administered intraperitoneally. As used herein, the abbreviation "i.v." means that anti-substance P antibodies, or anti-substance P antibody fragments, were administered intravenously.

The phrases "parenteral administration" and "administered parenterally" as used herein mean modes of administration other than enteral administration, usually by injection, and includes, without limitation, intraarterial, intraarticulare, intracapsular, intracardiac, intradermal, intramuscular, intraorbital, intraperitoneal, intraspinal, intrasternal, intrathecal, intravenous, subcutaneous, subcuticular, subarachnoid, subcapsular, and transtracheal injection and infusion.

As used herein, the phrase "inflammation-related diseases" means a disease or disorder which is caused in part or entirely by an inflammatory response in a subject due to a variety of diseases or syndromes, wherein the inflammatory response may be produced in part or entirely by the activity of substance P, and wherein the disease or disorder may be prevented or treated by inhibiting in part of whole the activity of substance P. Examples of viral or bacterial pathogenic agents, or conditions, that induce an inflammatory response that is the subject of this invention include, by way of nonlimiting example, respiratory syncytial virus, cytomegalovirus-associated allograft rejection, hepatitis B virus and chronic hepatitis, viruses that induce T cell activation, staphylococcal enterotoxin B, bacterial superantigens, bacterial endotoxin, bacterial sepsis, cardiopulmonary bypass, and multiple sclerosis lesions.

The phrase "pharmaceutically acceptable" is employed herein to refer to those compounds, materials, compositions, and/or dosage forms which are, within the scope of sound medical judgement, suitable for use in contact with the fluids and tissues of subjects without excessive toxicity, irritation, allergic response, or other problem, complication, or undesirable biological effect, and without interacting in a deleterious manner with other components which may be present in a pharmaceutical composition containing such components, materials, compositions and/or dosage forms commensurate with a reasonable benefit/risk ratio.

The phrase "pharmaceutical carrier" as used herein means a pharmaceutically-acceptable material, composition or vehicle, such as a liquid or solid filler, diluent, excipient, solvent or encapsulating material, involved in carrying or transporting an active agent, such as anti-substance P antibodies, or anti-substance P antibody fragments, from one organ, or portion of a subject's body, to another organ, or portion of a subject's body. Some examples of materials which can serve as pharmaceutical carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "purified" in relation to anti-substance P antibodies and anti-substance P antibody fragments means that the anti-substance P antibodies and anti-substance P antibody fragments are of sufficient purity so that they may be employed, and will function properly, in the methods of the present invention, as well as in clinical, diagnostic, experimental or other procedures. Many procedures are known by those of ordinary skill in the art for purifying antibodies and antibody fragments prior to their use in other procedures. The term "purified" as used herein in relation to substance P means that the substance P is of sufficient purity so that it may bind with antibodies, or antibody fragments, which have the ability to bind with substance P.

As used herein, the term "subject" includes humans and animals, particularly mammals.

The phrase "pharmaceutically-effective amount" as used herein means that amount of anti-substance P antibodies, or anti-substance P antibody fragments, which is effective for inhibiting the activity of at least some endogenous substance P, and which is effective for preventing an inflammation-related disease, as defined hereinabove, for treating an inflammation-related disease, as defined hereinabove (i.e., for eliminating the disease from the subject, or for reducing the effects of the disease in the subject), or for producing some other desired therapeutic effect in a subject, at a reasonable benefit/risk ratio applicable to any medical treatment.

Antibodies and Antibody Fragments. The anti-substance P antibodies, and anti-substance P antibody fragments, may be employed in the methods of the invention in pharmaceutically-effective amounts to prevent, or treat, inflammation-related diseases in a subject. The anti-substance P antibodies, and anti-substance P to antibody fragments, which may be employed in the methods of the present invention, have the ability to inhibit the action of endogenous substance P, for example, by binding to an epitope present on substance P and blocking substance P binding to cellular receptors for substance P, thereby preventing substance P from binding to such receptors, and exhibiting biological activity (i.e., neutralization of the substance P peptide by the antibodies, or antibody fragments).

The antibodies which may be employed in the methods of the invention may be polyclonal or monoclonal, and the antibody fragments which may be employed in these methods may be derived from polyclonal or monoclonal antibodies. Polyclonal and monoclonal antibodies may be prepared by methods which are well-known by those of skill in the art. See, for example, Harlow and Lane, *Antibodies: A Laboratory Manual*, Cold Spring Harbor Laboratory, Cold Spring Harbor, N.Y. (1988). For the production of polyclonal antibodies, purified substance P can be injected into an animal in an amount, and in intervals, sufficient to elicit an immune response (i.e., the production of antibodies against the substance P). Such polyclonal antibodies can be obtained from the animal by standard methods, and purified directly by well-known methods.

Monoclonal antibodies are generally preferred, however, due to their highly specific nature for a particular epitope on an antigen. For the production of monoclonal antibodies, spleen cells can be removed from an animal which has been injected several times over a period of time with an amount of substance P which is sufficient to elicit an immune response in the animal, fused with an immortal cell line (rapidly-dividing myeloma cells), placed into wells, grown, and screened for the production of monoclonal antibodies to a particular epitope present on substance P. For additional information concerning the preparation of monoclonal antibodies against substance P, see Couraud et al., "Monoclonal Antibodies to Substance P; Production, Characterization of their Fine Specificities, and Use in Immunocytochemistry," *Journal of Neurochemistry* 49:1708 (1987).

Because substance P and neurokinin A have a structurally similar carboxyl sequence, in order to increase the specificity of antibodies generated against substance P (the ability of the antibodies to bind to substance P, but not to neurokinin A), and antibody fragments thereof, it is preferable to generate the antibodies against the N-terminal portion of the substance P amino acid sequence, rather than against the C-terminal portion of the sequence. It is preferable that the antibodies, and antibody fragments, employed in the methods of the invention do not cross react with the related peptides neurokinin A and neurokinin B, so that their binding occurs with epitopes present on endogenous or exogenous substance P, and not with epitopes present on neurokinin A or neurokinin B.

Many procedures are known by those of ordinary skill in the art for purifying antibodies and antibody fragments from other proteins, contaminants, and materials with which they may normally be associated prior to their use in various procedures. For example, Jafarian et al., "Passive Immunization with an Anti-Substance P Antibody Prevents Substance P- and Neurokinin A-Induced Bronchospasm in Anesthetized Guinea Pigs," supra., describes the purification of anti-substance P monoclonal antibodies from culture supernatant using three chromatographic methods: protein A-sepharose, protein G-sepharose and thiophilic gel.

Numerous well-known assay techniques based upon immunological reactions between antigens and antibodies may be performed using substance P as the antigen to determine whether or not a particular antibody, or antibody fragment, has the ability to bind to an epitope present on the substance P, and to potentially inhibit the activity of endogenous substance P. These techniques include the enzyme-linked immunosorbent assays (ELISA), immunofluorescence assays (IFA), radioimmuno assays, immunoelectrophoreses, immunoblotting and the like. For example, Jafarian et al., supra., describe an inhibition assay which was employed to estimate the relative affinities of an anti-substance P monoclonal antibody derived from the rat-mouse heterohybridoma NC1/34 for substance P, neurokinin A and calcitonin gene-related peptide. Using any of the known assay techniques which are based upon immunological reactions, the ability of particular antibodies, or antibody fragments, to bind with substance P may be determined by contacting a fluid, solid or other medium which contains substance P with purified antibodies, or antibody fragments, and detecting the presence of binding between the antibodies, or antibody fragments, and the substance P. The presence of binding indicates the ability of the antibodies, or antibody fragments, to bind with the substance P. Preferably, the antibodies, or antibody fragments, employed in the methods of the invention will be specific for substance P (i.e., they will bind to an epitope present on substance P which is not common to other related proteins, or to other molecules, and will bind with a higher affinity to substance P than to other antigens).

The various epitopes which may be present on substance P, and with which an antibody, or antibody fragment, may bind, can be readily determined using the well-known techniques of epitope mapping and conformational dependency analysis. The activity of a particular antibody or antibody fragment produced may be determined by its ability to inhibit the action of substance P. In making such a determination, one first needs to associate substance P with the inflammatory disease by assaying for systemic or local increases in substance P in a subject. At least two methods are available for determining inhibitory effectiveness of an antibody or antibody fragment. In one method, anti-substance P antibodies or fragments may be tested in vitro for their ability to inhibit substance P by examining the dose-response effect of adding the antibody or fragment to cultures of lymphocytes, such as peripheral blood lymphocytes. Using a flow cytometer, one could then readily assess whether there was an inhibition of intracellular cytokines at various time-points after treatment. In a second method, one may administer one or more pharmacological doses of an anti-substance P antibody in vivo in a mouse model, either locally or systemically, to inhibit the actions of substance P. Inhibition of substance P would result in an inhibition or change in the type of inflammatory response. Quantitating levels of proinflammatory cytokines in inflammatory cells could assess a change in the type of inflammatory response. Furthermore, additional assays for substance P or the cytokines whose levels it modulates may be performed by methods such as Western blot analysis, ELISA, affinity chromatography, immunoprecipitation, competitive inhibition analysis, and the like.

To determine whether a particular antibody, or antibody fragment, has the ability to prevent or treat an inflammation-related disease, the mouse model discussed in the preceding paragraph may be studied. In such determinations, a mouse may be infected with an inflammation-producing pathogen. The procedures outlined above may be applied to evaluate the ability to prevent (if administered before infection) or treat (if administered after infection) the inflammation associated with the pathogen.

Antibody fragments, such as $F(ab)_2$ fragments, may be prepared from polyclonal or monoclonal antibodies by standard methods known by those of skill in the art. For example and in brief, an antibody is incubated with pepsin in a buffer of 100 mM sodium citrate, pH 3.5, at 37° C. for 24 h. The digestion is terminated by adding 3 M Tris buffer pH 8.8. The $F(ab)_2$ fragments are resolved from the Fc fragments by chromatography over a protein A column, which selectively binds Fc fragments. The $F(ab)_2$ fragments are collected in the flow through fractions.

Conventional techniques of molecular biology which may be employed in producing anti-substance P antibodies, and anti-substance P antibody fragments, and in generally carrying out the methods of the present invention, are fully explained in the literature. See, for example, Rose et al., *Manual of Clinical Laboratory Immunology*, 5th ed., Eds. American Society for Microbiology, Washington (1996); Harlow and Lane, *Antibodies: A Laboratory Manual*, supra.; Roitt et al., *Immunology*, The C.V. Mosby Company, St. Louis, Mo. (1985); Kuby, *Immunology*, W.H. Freeman and Co., New York (1992); Ausubel et al., Current Protocols in Molecular Biology, Green Publishing Associates and Wiley-Interscience, John Wiley and Sons, New York (1987; updated quarterly); Sambrook et al., *Molecular Cloning—A Laboratory Manual*, Cold Spring Harbor Laboratory, Cold Spring Harbor, N.Y. (1985); Davis et al., *Basic Methods in Molecular Biology*, Elsevier Science Publishing Co., Inc., New York (1986); Rodriguez et al., *Recombinant DNA Techniques: An Introduction*, The Benjamin/Cummings Publishing Company, Inc., Menlo Park, Calif. (1983); and Maniatis et al., *Molecular Cloning: A Laboratory Manual*, Cold Spring Harbor, N.Y. (1982).

Dosage and Mode of Administration. The methods of the present invention are useful for preventing and/or treating inflammation-related diseases in a subject. A physician or veterinarian of ordinary skill in the art can readily determine whether or not a particular subject has an inflammation-related disease, or is particularly susceptible to an inflammation-related disease.

While anti-substance P antibodies, and anti-substance P antibody fragments, may be employed in the methods of the invention alone, they will preferably be employed in the form of a pharmaceutical composition or formulation. For human subjects or patients, these antibodies, fragments and pharmaceutical compositions should be used under the guidance of a physician.

The pharmaceutical compositions which may be employed in the methods of the invention will typically comprise one or more types of anti-substance P antibodies, and/or anti-substance P antibody fragments, as an active ingredient in admixture with one or more pharmaceutically-acceptable carriers and, optionally, with one or more other types of antibodies, antibody fragments, compounds, drugs, therapeutic agents or other materials. The appropriate dosage and mode of administration of the anti-substance P antibodies, anti-substance P antibody fragments and pharmaceutical compositions which may be employed in the methods of the invention should be suitably selected by methods which are consistent with conventional pharmaceutical practices.

The anti-substance P antibodies, anti-substance P antibody fragments and pharmaceutical compositions which may be employed in the methods of the invention may be specifically formulated for oral administration in solid or liquid form, for parenteral injection, for rectal or vaginal administration or for topical administration. They may be administered to humans and other subjects for the prevention or therapy of inflammation-related diseases by any suitable route of administration, including orally, nasally, as by, for example, a spray, rectally, intravaginally, parenterally, intracisternally or topically, as by powders, ointments and drops, including bucally and sublingually. Preferably the antibodies are administered via a parenteral route.

Regardless of the route of administration, the anti-substance P antibodies, anti-substance P antibody fragments and pharmaceutical compositions which may be employed in the methods of the invention are formulated into pharmaceutically-acceptable dosage forms by conventional methods known by those of skill in the art.

Actual dosage levels of the active ingredients employed in the methods of the invention may be varied so as to obtain an amount of the active ingredient which is effective to achieve the desired preventative effect, or therapeutic response, for a particular subject, composition, and mode of administration, without being toxic to the subject. The selected dosage level will depend upon a variety of factors, including the activity of the particular anti-substance P antibodies or anti-substance P fragments being employed, the route of administration, the time of administration, the rate of excretion of the particular antibodies or fragments being employed, the severity of the disease, the duration of the treatment, other drugs, therapeutic agents or materials which are being used in combination with the particular antibodies or fragments being employed, the species, age, sex, weight, condition, general health and prior medical history of the subject being treated, and like factors which are well known in the medical arts. A physician or veterinarian having ordinary skill in the art can readily determine and prescribe the effective amount of anti-substance P antibodies, anti-substance P antibody fragments or a pharmaceutical formulation containing such antibodies or antibody fragments required to prevent or treat an inflammation-related disease. For example, in order to treat a particular inflammation-related disease, the physician or veterinarian could start doses of the anti-substance P antibodies, anti-substance P antibody fragments or pharmaceutical composition containing the antibodies or antibody fragments at levels which are lower than that required in order to achieve the desired therapeutic effect, and gradually increase the dosage until the desired therapeutic effect in achieved.

In general, a suitable daily dose of anti-substance P antibodies, anti-substance P antibody fragments or a pharmaceutical composition containing these antibodies or fragments will be at least that amount of the antibodies, antibody fragments or pharmaceutical composition which is the lowest dose which is effective to produce a therapeutic effect. Pharmaceutically-effective amounts of the anti-substance P antibodies, anti-substance P antibody fragments and pharmaceutical compositions containing these antibodies and fragments for a particular subject may be determined using standard procedures. Generally, dosage levels which range from about 0.5 mg/kg body weight to about 2 g/kg body weight, and more preferably range from about 1 mg/kg body weight to about 1 g/kg body weight, and still more preferably range from about 5 mg/kg body weight to about 100 mg/kg body weight, of the anti-substance P antibodies, or anti-substance P antibody fragments, per day are administered to a mammalian subject. However, the total daily usage of the anti-substance P antibodies, or anti-substance P antibody fragments, or of the pharmaceutical compositions comprising such active agents, will be determined by an attending physician or veterinarian within the scope of sound medical judgement.

If desired, the effective daily dose of the anti-substance P antibodies or anti-substance P antibody fragments may be administered as two, three, four, five, six or more sub-doses administered separately at appropriate intervals throughout the day, optionally, in unit dosage forms. Such a multiple dosage regime allows for the observation of the patient after each dose and, if appropriate, modification of the dosage amount and/or regime.

The pharmaceutical compositions which may be employed in the methods of the invention comprise anti-substance P antibodies, or anti-substance P antibody fragments, together with one or more pharmaceutically-acceptable carriers thereof and, optionally, with other therapeutic agents. Each carrier should be "acceptable" in the sense of being compatible with the other ingredients of the formulation, and not injurious to the patient. Wetting agents, emulsifiers and lubricants, such as sodium lauryl sulfate and magnesium stearate, as well as coloring agents, release agents, coating agents, preservatives, antioxidants, and the like can also be employed in the pharmaceutical compositions used in the methods of the invention.

Formulations of the anti-substance P antibodies and anti-substance P antibody fragments used in the methods of the invention may be conveniently prepared in a unit dosage form, and may be prepared by any of the numerous methods which are well known in the art of pharmacy. The amount of active ingredient (anti-substance P antibodies or fragments) which can be combined with a carrier material to produce a single dosage form will vary depending upon the patient being treated, the particular mode of administration and all of the other factors described above. The amount of active ingredient which can be combined with a carrier material to produce a single dosage form will generally be that amount of the active ingredient which is the lowest dose which is effective to produce a therapeutic effect. Generally, out of one hundred percent for the pharmaceutical formulation, this amount will range from about one to about ninety-nine percent of active ingredient, preferably from about five to about seventy percent of active ingredient, and most preferably from about ten to about thirty percent of active ingredient.

Methods for preparing the pharmaceutical compositions which may be employed in the methods of the invention include the step of bringing into association the active ingredient with the carrier and, optionally, with one or more accessory ingredients, and then, if necessary, shaping the product. Formulations of the active ingredient which are suitable for oral administration may be in the form of capsules, cachets, pills, tablets, lozenges, powders, granules, solutions or suspensions in an aqueous or nonaqueous liquid, or oil-in-water or water-in-oil emulsions. Formulations of the active ingredient for rectal or vaginal administration may be in the form of a gel, cream, foam or suppository, which may be prepared by mixing the active ingredient with one or more non-irritating excipients or carriers comprising, for example, cocoa butter, polyethylene glycol, a suppository wax or a salicylate. They will preferably be solid at room temperature, but liquid at body temperature, so that they will melt in the rectum or vaginal cavity of the subject and release the active ingredient. Dosage forms for the topical or transdermal administration of the active ingredient include powders, sprays, ointments, pastes, creams, lotions, gels, solutions, patches and inhalants.

Pharmaceutical compositions containing anti-substance P antibodies and/or anti-substance P antibody fragments which may be employed in the methods of the invention, and which are suitable for parenteral administration, comprise one or more types of anti-substance P antibodies and/or anti-substance P antibody fragments in combination with one or more pharmaceutically-acceptable carriers. Such carriers may be sterile, isotonic, aqueous or nonaqueous solutions, dispersions, suspensions or emulsions, or sterile powders which may be reconstituted into sterile injectable solutions or dispersions just prior to use. These pharmaceutical formulations may contain antioxidants, buffers, bacteriostats, solutes that render the formulation isotonic with the blood of the intended recipient and/or suspending or thickening agents. Examples of suitable aqueous and nonaqueous carriers which may be employed in these compositions include water, ethanol, polyols (glycerol, propylene glycol, polyethylene glycol, and the like, and suitable mixtures thereof), vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

In some cases, in order to prolong the effect of an active ingredient, it is desirable to slow the absorption of an active ingredient administered by, for example, subcutaneous or intramuscular injection. This may be accomplished by the use of a liquid suspension of a material having poor water solubility. The rate of adsorption of the active ingredient will then depend upon its rate of dissolution. Delayed adsorption of a parenterally-administered active ingredient may also be accomplished by dissolving or suspending the active ingredient in an oil vehicle. In addition, prolonged absorption of the injectable pharmaceutical form may be brought about by the inclusion of agents which delay absorption, such as aluminum monostearate and gelatin.

Forming microencapsule matrices of the active ingredient in biodegradable polymers, such as polylactide-polyglycolide, may make injectable depot forms of the active ingredient. Depending upon the ratio of the active ingredient to polymer employed, and the nature of the particular polymer employed, the rate of release of the active ingredient can be controlled. Examples of other biodegradable polymers include poly(orthoesters) and poly(anhydrides). Depot injectable formulations may also be prepared by entrapping the active ingredient in liposomes or microemulsions which are compatible with body tissue.

Materials which may be used to prepare an injectable pharmaceutical formulation of anti-substance P antibodies and anti-substance P antibody fragments can be sterilized, for example, by filtration through a bacterial-retaining filter, or by incorporating sterilizing agents in the form of sterile solid compositions which can be dissolved or dispersed in sterile water, or in other sterile injectable media, into the formulations just prior to use. Injectable pharmaceutical formulations containing anti-substance P antibodies or anti-substance P antibody fragments may be present in unit-dose or multi-dose sealed containers, such as ampoules and vials, and may be stored in a lyophilized condition requiring only the addition of the sterile liquid carrier, for example, water, immediately prior to use. All of the pharmaceutical formulations discussed may be prepared using standard pharmaceutical techniques which are well-known to those skilled in the art.

The following examples describe and illustrate the methods of the invention. These examples are intended to be merely illustrative of the present invention, and not limiting thereof in either scope or spirit. Those of skill in the art will readily understand that variations of the materials used in, and the conditions and processes of, the procedures described in these examples can be used. All materials and equipment employed in the examples, and generally employed to practice the methods of the invention, are commercially available. Sources for these materials and equipment are set forth in the examples, or are known by those of skill in the art.

EXAMPLE 1

Quantification of Substance P Levels in Mouse Bronchoalveolar Lavage Specimens

In these experiments, the levels of substance P in cell-free bronchoalveolar lavage (BAL) fluid specimens collected from BALB/c mice i.n. infected with $10^6$ pfu of respiratory syncytial virus during the acute immune response to the virus at various timepoints post infection were quantitated by competitive enzyme immunoassay (ELISA).

The competitive ELISA performed is based upon the competition between free substance P (Biomol Research Laboratories, Plymouth Metting, PA) and a substance P tracer (Cayman Chemical, Ann Arbor, Mich.) for a limited number of substances P-specific antibody binding sites. Dilutions of bronchoalveolar lavage fluid were analyzed against a substance P standard, and the results were calculated as the percent of sample or standard bound, and the maximum bound. Intra- and interassay coefficients of variation (CV) were less than or equal to 10 percent.

Four- to six-week old specific pathogen-free female BALB/c mice (Harlan Sprague Dawley, Indianapolis, Ind.) were anesthetized with avertin (2,2,2,-tribromoethanol, Aldrich Chemical Co., Milwaukee, Wis.). The lungs were washed via a catheter inserted through a tracheal incision with 1 ml of phosphate buffered saline (GIBCO Laboratories, Grand Island, N.Y.). The responses of three mice were examined for each time-point, and the mean values reported.

Figure 1:
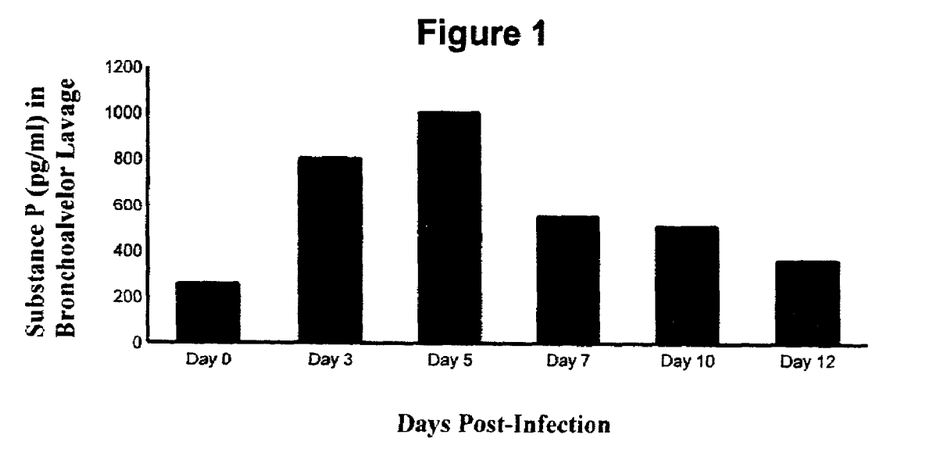
FIG. 1 is a graph for the amount of substance P present in bronchoalveolar lavage fluid obtained from the lungs of BALB/c mice which had been infected with respiratory syncytial virus versus the number of days post-infection. This graph is derived from the data from Example 1.

The inflammatory response in the lungs of the mice peaked between days 3 and 7 post-infection with the respiratory syncytial virus. Compared with naïve mice (i.e., uninfected mice), the inflammatory response in the lungs of the BALB/c mice was characterized by an approximately 50-fold increase in cell numbers in the lung, of which macrophages constitute about 60%, lymphocytes about 30%, and polymorphonuclear cells about 10%. $CD4^+$ T lymphocytes produced peak levels of intracellular cytokines IL-2, IL-4 and IL-6 at day 3 post infection, and IL-5 and IFNγ levels peaked at day 5 post-infection. $CD8^+$ T lymphocytes also participated in the cytokine-mediated inflammatory response to respiratory syncytial virus, but at a lesser magnitude. All cytokines decreased to near baseline (levels at day 0) by day 12 post-infection. The T lymphocyte response to respiratory syncytial virus was predominantly characterized by a Th1-type mRNA cytokine pattern (IL-2, IFNγ) in the BALB/c mice. That is, only Th 1-type cytokine mRNA (which may include mRNA for IFNγ, IL-2, IL-12, and lymphotoxin mRNAs) is found. This pattern is the same as occurs with humans. FIG. 1 shows that changes in levels of substance P found in the cell-free bronchoalveolar lavage fluid follow a pattern very similar to that for cell numbers and intracellular cytokine levels. FIG. 1 shows that substance P levels in the bronchoalveolar lavage fluid rise from a baseline of about 250 pg/mL at day 0 (naïve mice) to about 800 pg/ml by day 3 post infection, peak at about 1000 pg/mL on day 5 post infection, and then rapidly decline to about 350 pg/mL at day 12 post infection.

EXAMPLE 2

Examination of the Impact of Exogenous Substance P on $CD4^+$ and $CD8^+$ T Lymphocyte Proliferation In order to better understand how substance P directly affects the immune response, the effect of exogenous substance P on the proliferation of intact, or unfractionated, T lymphocytes, and of CD4+ and CD8+ enriched T lymphocyte populations, induced with the mitogens (substances which induce mitosis and cell transformation, especially lymphocyte transformation) concanavalin and lipopolysaccharide in BALB/c mice was examined. T lymphocytes, isolated from three pooled spleens of BALB/c mice were enriched with CD4+ and CD8+ T lymphocytes by standard methods using streptavidin-coated magnetic beads (Dynal A S., Oslo, Norway) coupled to biotin-anti-CD8a (53-6.7, PharMingen, San Diego, Calif.), or to biotin-anti-CD4 (RM4–5, PharMingen). A portion of the CD4+ and CD8+ T lymphocytes were analyzed by flow cytometry using an FACScan (Becton-Dickinson, Mountain View, Calif.) and found to be enriched to greater than 95 percent using magnetic beads.

Figure 2:
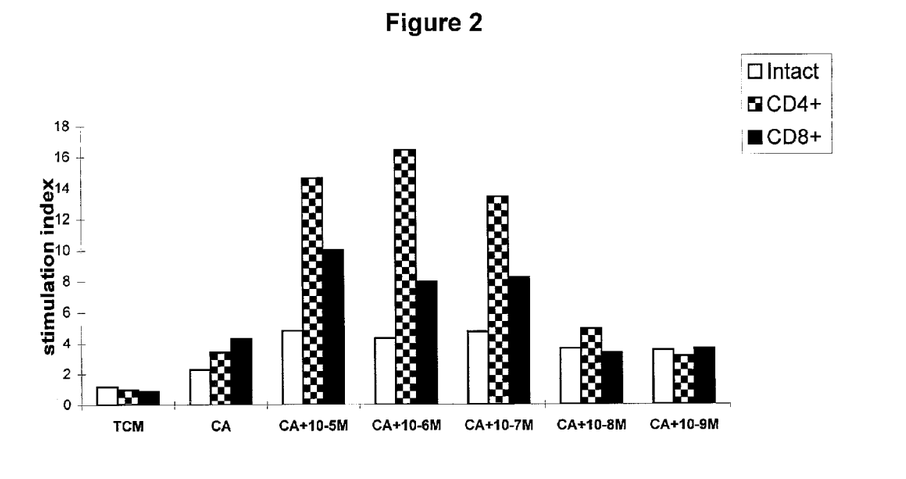
Figure 3:
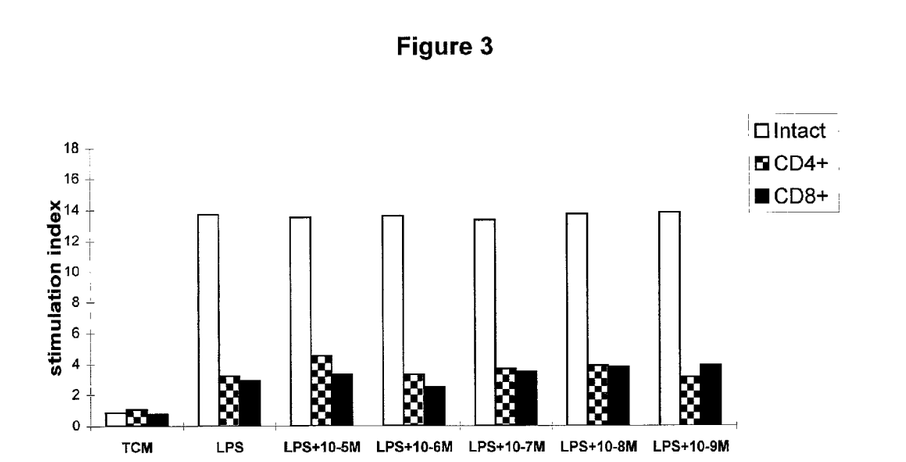

Intact, and CD4+ and CD8+ enriched, T lymphocytes were stimulated with the mitogen concanavalin (Sigma Chemical Co., St. Louis, Mo., 2 µg/mL; FIG. 2) or lipopolysaccharide (Sigma Chemical Co., St. Louis, Mo., 100 µg/mL; FIG. 3), with or without the addition of concentrations of substance P (Biomol Research Laboratories) ranging from $10^{-5}$ M to $10^{-9}$ M, or were left unstimulated in tissue culture medium (GIBCO) containing 10% heat-inactivated FBS (Hyclone Laboratories, Logan, Utah) plus 1% of antibiotic/antimycotic (GIBCO BRL, Grand Island, N.Y.). Substance P was added to the cell cultures of intact, and CD4+ or CD8+ enriched, T lymphocytes at concentrations comparable to those found in bronchoalveolar lavage fluid ($10^{-5}$ M to $10^{-9}$ M). Cells were cultured at 37° C. for 48 hours, and all of the wells for the cells were pulsed with 1 µCi of tritiated thymidine (Amersham, Arlington Heights, Ill.) for 25 hours, and then harvested with a Matrix Cell Harvester (Packard Instruments, Meriden, Conn.).

The results of these experiments are shown in FIGS. 2 and 3. The stimulation index is the mean counts per minute (cpm) of stimulated, or experimental, cells divided by the mean counts per minute of unstimulated, or control, cultures (intact, CD4+ or CD8+ T lymphocytes which were left unstimulated in tissue culture medium). A statistically significant value of the stimulation index above 1.0 indicates a significant effect of the experimental parameter above that of control.

The exogenous addition of substance P at concentrations from $10^{-5}$ M to $10^{-9}$ M to the intact T lymphocytes did not induce any detectable increase in cell proliferation. In contrast, and as is shown in FIGS. 2 and 3, CD4+ T lymphocytes stimulated with concanavalin (FIG. 2), but not CD4+ T lymphocytes stimulated with lipopolysaccharide (FIG. 3), showed a 7- to 8-fold increase in proliferation when cocultured with substance P at concentrations ranging from $10^{-5}$ M to $10^{-7}$ M. CD8+ T lymphocytes stimulated with concanavalin A showed a 4- to 5-fold increase in proliferation. These data suggest that activated T lymphocytes are more sensitive to substance P than are naïve or quiescent lymphocytes, and that CD4+ T lymphocytes are more sensitive to substance P than are CD8+ T lymphocytes.

To confirm the specificity of substance P-induced cell proliferation, rabbit anti-substance P antibody (PharMingen) was added to a portion of the cell cultures containing concanavalin and substance P during incubation. Enhanced cell proliferation caused by the addition of substance P was found to be inhibited by the addition of 100 µg rabbit anti-substance P antibody to each culture. Further, no effect of rabbit anti-substance P antibody was observed on cell cultures only stimulated with mitogens (i.e., not with substance P).

EXAMPLE 3

Treatment of Mice Infected with Respiratory Syncytial Virus with Anti-Substance P Antibody Fragments In order to ascertain the connection of substance P with cytokine-based inflammation caused by respiratory syncytial virus infection, BALB/c mice, which were acutely infected with respiratory syncytial virus were i.n. treated with rabbit anti-substance P F(ab)$_2$ antibody fragments to inhibit the biological activity of substance P. An anti-substance P F(ab)$_2$ antibody fragment dose-response experiment was also performed in order to determine the amount of the antibody fragments which was required to block the effects of substance P on the intracellular generation of cytokines by CD3+ T lymphocytes. The effect of the rabbit anti-substance P F(ab)$_2$ antibody fragments on intracellular cytokine production by T lymphocytes isolated from the lungs was also examined.

Rabbit anti-substance P antibodies (PharMingen) were incubated overnight at 37° C. in citrate buffer containing 5 µg of pepsin (Sigma Chemical Company) per 1 µg of antibody. The antibodies were then centrifuged at 10,000 G for 30 minutes, resuspended in phosphate buffered saline (GIBCO), and run over a protein A column (Sigma Chemical Company) to separate anti-substance P F(ab)$_2$ antibody fragments from anti-substance P Fc antibody fragments.

BALB/c mice (Harlan Sprague Dawley) were i.n. infected with $10^6$ pfu of respiratory syncytial virus (Long, A strain), and then rested for three days. The mice were then anesthetized with avertin (Aldrich Chemical Co.), and i.n. treated with 2, 20 or 200 µg per mouse of rabbit anti-substance P F(ab)$_2$ antibody fragments or with 200 µg per mouse of normal rabbit Ig (nIg) antibodies. Controls were not treated. This treatment was given to the mice during the peak of intracellular cytokine production by T lymphocytes, which occurs on day 4 post-infection with the respiratory syncytial virus.

T lymphocytes were collected from bronchoalveolar lavage specimens obtained from the mice either 18 hours (FIG. 4) or 36 hours (FIG. 5) after treatment with the rabbit anti-substance P F(ab)$_2$ antibody fragments, or with normal rabbit Ig antibodies, and were stained for the observation of intracellular cytokines in order to examine the levels of intracellular cytokines produced by the T lymphocytes 18 hours and 36 hours post-treatment. The procedure used for immunofluorescence intracellular cytokine staining was modified from the protocol described by PharMingen. Briefly, the intracellular transport of cytokines in the T lymphocytes was inhibited using 1 µg/mL brefeldin (Sigma Chemical Company). The T lymphocyte cells were washed in phosphate buffered saline (GIBCO), and the cell surface antigen was stained with either anti-CD4+ (RM4-5) or anti-CD8+ (53-6.7) antibody, and subsequently fixed with 4% paraformaldehyde (Ted Pella Inc., Redding, Calif.) in D-phosphate buffered saline containing 1% bovine serum albumin. The cells were washed in phosphate buffered saline, and the membranes were permeabilized using saponin (Sigma Chemical Company). All intracellular antibodies were labeled with phycoerythrin, and were purchased from PharMingen. Anti-IL-2 (JES6-5H4), anti-IL-4 (BVD4-1D11), anti-IL-5 (TRFK5), anti-IL-6 (MP5-20F3), and anti-IFNγ (XMG1.2) antibodies were diluted in D-phosphate buffered saline containing 1% bovine serum albumin and 0.1% saponin. The cells were stained on ice using an appropriate amount of the intracellular antibody (equivalent to 1 µg/mL), washed phosphate buffered saline, resuspended in D-phosphate buffered saline containing 1% bovine serum albumin, and analyzed by flow cytometry using an FACScan (Becton-Dickinson).

Figure 4:
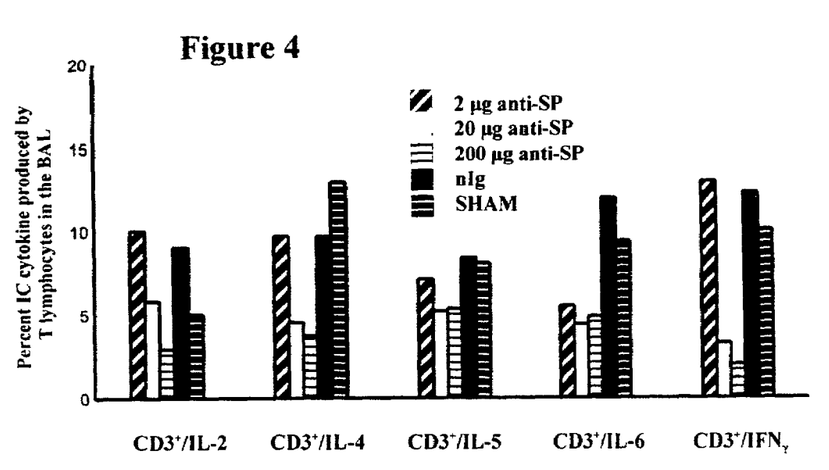
Figure 5:
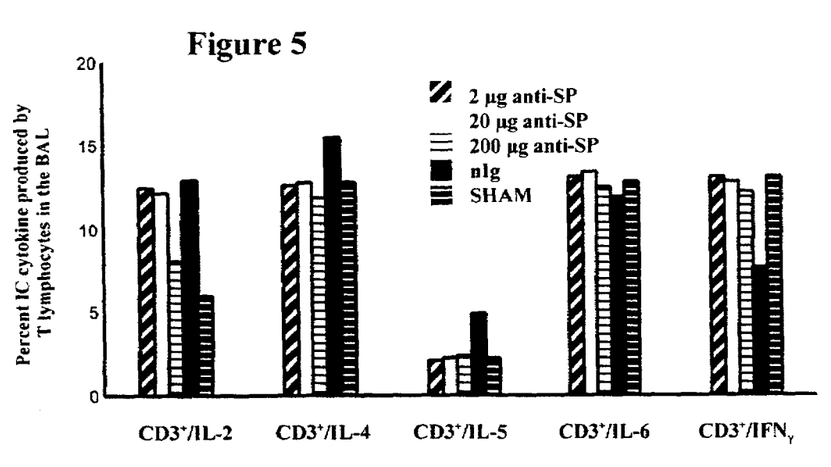
FIG. 5 shows a graph which plots the percent of intracellular cytokines produced by T lymphocytes in the bronchoalveolar lavage fluid of BALB/c mice infected with respiratory syncytial virus collected 36 hours after the mice were treated with rabbit anti-substance P $F(ab)_2$ antibody fragments on the vertical axis, and the type of intracellular cytokine examined on the horizontal axis, for the experiments described in Example 3. The abbreviations and symbols appearing in FIG. 5 are defined in the same manner as for FIG. 4.

FIG. 4 shows that, at 18 hours post-treatment, a single i.n. treatment of 200 μg of the rabbit anti-substance P F(ab)$_2$ antibody fragments per mouse induced approximately a 3-fold reduction in the intracellular cytokines IL-2, IL-4, IL-6 and IFNγ made by T lymphocytes in the bronchoalveolar lavage fluid of the mice. The inhibitory effect of the rabbit anti-substance P F(ab)$_2$ antibody fragments on the intracellular cytokines was found to be dose dependent, and specific for T lymphocytes in the bronchoalveolar lavage fluid of the mice. (No effect of the rabbit anti-substance P F(ab)$_2$ antibody fragments on the levels of intracellular cytokines was observed in spleens obtained from the mice.) FIG. 4 also shows that less of an inhibitory effect of the rabbit anti-substance P F(ab)$_2$ antibody fragments on the levels of intracellular cytokines present in the bronchoalveolar lavage fluid of the mice was observed when 20 μg of the rabbit anti-substance P F(ab)$_2$ antibody fragments were administered. No inhibitory effect was observed when 2 μg of the rabbit anti-substance P F(ab)$_2$ antibody fragments were administered. FIG. 5 shows that, at 36 hours post treatment, the only detectable and significant inhibitory effect of the rabbit anti-substance P F(ab)$_2$ antibody fragments occurred for the production of the IL-2 cytokine by the T lymphocytes in the bronchoalveolar lavage fluid of the mice.

T lymphocytes were obtained from the bronchoalveolar lavage fluid of the infected BALB/c mice by inserting a catheter through a tracheal incision, and washing the lungs. T lymphocytes were analyzed by flow cytometry after binding labelled anti-CD3 MAb. Phenotypic analysis of the T lymphocytes was performed by cell surface staining the lymphocytes with phycoerythrin-conjugated MAbs specific for cell activation molecules such as CD49d or CD54, and assaying by flow cytometry. The results showed a reduction in the expression of inflammatory molecules, such as CD49d and CD54, on the surface of T lymphocytes following treatment of the mice with rabbit anti-substance P F(ab)$_2$ antibody fragments, as well as a decrease in the numbers of granular cells.

The data resulting from these experiments show that inhibiting the biological activity of endogenous substance P found in bronchoalveolar lavage fluid obtained from mice infected with respiratory syncytial virus, with anti-substance P antibody fragments, can reduce the levels of intracellular cytokine production by T lymphocytes present in the lungs, and beneficially modify the immune response to infection by respiratory syncytial virus. The magnitude of the inhibition of intracellular cytokine production by T lymphocytes in the bronchoalveolar lavage fluid of the BALB/c mice by administration to the mice of rabbit anti-substance P F(ab)$_2$ antibody fragments suggests that this treatment may have broad effects on the immune and inflammatory response to respiratory syncytial virus infection.

Similar experiments were performed to those described hereinabove, with the exception that the anti-substance P F(ab)$_2$ antibody fragments were administered to the mice either by i.v. or i.p. routes. The data resulting from these experiments demonstrated that treatment of the mice with the anti-substance P F(ab)$_2$ antibody fragments inhibited the production of intracellular cytokines. The results of the anti-substance P treatment were found to be rapid (i.e., occurring within eighteen hours), to be persistent (i.e., having an effect up to seventy-two hours post-treatment for IL-2 and IL-4), and to operate in a dose-dependent manner. These data suggest that the results observed are specific, and are attributable to the anti-substance P treatment. In addition, it was observed that the i.p. administration of the anti-substance P F(ab)$_2$ antibody fragments appeared to have a slightly stronger effect at inhibiting the production of intracellular cytokines when compared to either i.n. or i.v. routes of administration. Consistent with these observations are results which were obtained from the histological examination of bronchoalveolar fluid from the lungs of BALB/c mice obtained at various time points post treatment with the anti-substance P F(ab)$_2$ antibody fragments. These data showed that i.p. treatment with anti-substance P antibody fragments induced the least accumulation of inflammatory cells (e.g., eosinophils and polymorphonuclear cells) in the bronchoalveolar fluid, when compared to i.n. or i.v. treatment.

The foregoing examples are provided to enable one of ordinary skill in the art to practice the present invention. These examples are merely illustrative, however, and should not be read as limiting the scope of the invention as it is claimed in the appended claims. While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the invention be limited only by the scope of the claims which follow. Specific anti-substance P antibodies and anti-substance P antibody fragments, and methods, within the scope of the invention include, but are not limited to, the anti-substance P antibodies and anti-substance P antibody fragments, and methods, described herein. Contemplated equivalents of the anti-substance P antibodies and anti-substance P antibody fragments, and methods, described herein include anti-substance P antibodies and anti-substance P antibody fragments, and methods, which otherwise correspond thereto, and which have the same general properties thereof, wherein one or more simple variations are made which do not adversely affect the function of the anti-substance P antibodies and anti-substance P antibody fragments, and methods, described herein.

Throughout this application, various patents, publications, books, and amino acid sequences have been cited. The entireties of each of these patents, publications, books, and amino acid sequences are hereby incorporated by reference into this application.

What is claimed is:

1. A method for treating viral or bacterial-induced inflammation of the lung in a subject mediated by endogenous substance P, comprising nasally administering to the subject a pharmaccutically-effective amount of anti-substance P antibody fragments, thereby treating the viral or bacterial-induced inflammation of the lung in the subject.

2. The method of claim 1 wherein the inflammation of the lung is caused by a viral agent.

3. The method of claim 2 wherein the inflammation of the lung is caused by respiratory syncytial virus.

4. The method of claim 1 wherein from about 0.5 mg to about 2 g per kilogram of body weight per day of the antibody fragments are administered to the subject.

5. The method of claim 4 wherein from about 1 mg to about 1 g per kilogram of body weight per day of the antibody fragments are administered to the subject.

6. The method of claim 1 wherein anti-substance P F(ab')$_2$ antibody fragments are administered to the subject.

7. A method for treating viral or bacterial-induced bronchiolitis in a subject mediated by endogenous substance P, comprising nasally administering to the subject a pharmaceutically-effective amount of anti-substance P antibody fragments, thereby treating the viral or bacterial-induced bronchiolitis in the subject.

8. The method of claim 7 wherein the bronchiolitis is caused by a viral agent.

9. The method of claim 8 wherein the bronchiolitis is caused by respiratory syncytial virus.

10. The method of claim 7 wherein from about 0.5 mg to about 2 g per kilogram of body weight per day of the antibody fragments are administered to the subject.

11. The method of claim 10 wherein from about 1 mg to about 1 g per kilogram of body weight per day of the antibody fragments are administered to the subject.

12. The method of claim 7 wherein anti-substance P F(ab')$_2$ antibody fragments are administered to the subject.

13. A method for reducing the levels of intracellular cytokines in a subject with bacterial or viral induced inflammation of the lung, comprising nasally administering to the subject a pharmaceutically-effective amount of anti-substance P antibody fragments, thereby reducing the levels of intracellular cytokines in the T lymphocytes of the subject with bacterial or viral induced inflammation of the lung.

14. The method of claim 13 wherein the cytokine is IL-2, IL-4, IL-6, or INFγ.

* * * * *